United States Patent [19]

Christopfel

[11] Patent Number: 5,753,217

[45] Date of Patent: May 19, 1998

[54] METHOD OF REDUCING ORAL MALODOR

[75] Inventor: William C. Christopfel, 501 Brimhall St., St. Paul, Minn. 55116

[73] Assignees: William C. Christopfel; M. E. Saremi, both of Minneapolis, Minn.

[21] Appl. No.: 696,405

[22] Filed: Aug. 14, 1996

[51] Int. Cl.$^6$ .............................. A01N 25/10; A01N 7/20
[52] U.S. Cl. .......................... 424/76.9; 424/53; 424/405; 424/643; 424/661
[58] Field of Search ..................... 424/76.9, 405, 424/643, 661, 53

[56] References Cited

U.S. PATENT DOCUMENTS

| | | | |
|---|---|---|---|
| Re. 34,065 | 9/1992 | Wainberg et al. | 252/104 |
| 113,820 | 4/1871 | Vique | 424/76.9 |
| 1,960,500 | 5/1934 | Longo | 424/76.9 |
| 3,271,242 | 9/1966 | McNicholas et al. | 424/76.9 |
| 3,591,515 | 7/1971 | Lovely | 424/76.9 |
| 4,689,215 | 8/1987 | Ratcliff | 424/53 |
| 4,696,811 | 9/1987 | Ratcliff | 424/53 |
| 4,786,492 | 11/1988 | Ratcliff | 424/53 |
| 4,788,053 | 11/1988 | Ratcliff | 424/53 |
| 4,792,442 | 12/1988 | Ratcliff | 424/53 |
| 4,793,989 | 12/1988 | Ratcliff | 424/53 |
| 4,808,389 | 2/1989 | Ratcliff | 424/53 |
| 4,818,519 | 4/1989 | Ratcliff | 424/53 |
| 4,851,213 | 7/1989 | Ratcliff | 424/53 |
| 4,855,135 | 8/1989 | Ratcliff | 424/127 |
| 4,886,657 | 12/1989 | Ratcliff | 415/53 |
| 4,889,714 | 12/1989 | Ratcliff | 424/53 |
| 4,902,498 | 2/1990 | Agricola et al. | 424/52 |
| 4,925,656 | 5/1990 | Ratcliff | 424/53 |
| 4,975,285 | 12/1990 | Ratcliff | 424/661 |
| 5,052,590 | 10/1991 | Ratcliff | 222/94 |
| 5,076,960 | 12/1991 | Hutchings et al. | 252/186 |
| 5,200,171 | 4/1993 | Ratcliff | 424/52 |
| 5,348,734 | 9/1994 | Ratcliff | 424/53 |
| 5,486,356 | 1/1996 | Yim | 424/76.1 |

*Primary Examiner*—Neil S. Levy
*Attorney, Agent, or Firm*—Kinney & Lange, P.A.

[57] ABSTRACT

A method of reducing oral malodor includes providing a solution of sodium chlorite and a metal ion capable of complexing with sulfur and applying the solution as mouth rinse.

3 Claims, No Drawings

METHOD OF REDUCING ORAL MALODOR

BACKGROUND OF THE INVENTION

The present invention relates to the use of sodium chlorite and a metal ion such as zinc capable of complexing with sulfur containing compounds for use in the reduction of oral malodor.

Oral malodor is the result of volatile sulfur compounds, carboxylic acids and amines. The malodorous compounds are generated primarily through putrifactive action of oral micro-organisms on sulfur containing amino acids, peptones or proteins found in the mouth. Such micro-organisms are readily available in saliva and dental plaque or may be derived from proteinaceous food particles trapped between the teeth, in the gingival crevice or adhering to the mucous membranes and the irregular surface of the tongue as well as exfoliated oral epithelium, food debris and the like. Studies have indicated that mouth odor not only comes from the posterior dorsal surface of the tongue but also from periodontal pockets. People with periodontal involvement have an attendant increase in oral malodor from disintegrated epithelial cells.

The following patents describe various solutions for the reduction of oral malodor:

| Inventor | Patent No. |
| --- | --- |
| Ratcliff | 4,689,215 |
| Ratcliff | 4,696,811 |
| Ratcliff | 4,786,492 |
| Ratcliff | 4,788,053 |
| Ratcliff | 4,792,442 |
| Ratcliff | 4,793,989 |
| Ratcliff | 4,818,519 |
| Ratcliff | 4,851,213 |
| Ratcliff | 4,855,135 |
| Ratcliff | 4,886,657 |
| Ratcliff | 4,889,714 |
| Agricola et al. | 4,902,498 |
| Ratcliff | 4,925,656 |
| Ratcliff | 4,975,285 |
| Ratcliff | 5,052,590 |
| Ratcliff | 5,200,171 |
| Ratcliff | 5,348,734 |

The Hutchings et al. U.S. Pat. No. 5,076,960 describes the use of sodium chlorite with at least one salt of a transition or post-transition metal for use as a deodorizer. Zinc chloride is described as one useful salt for use in association with sodium chlorite. The composition is useful as a deodorizer for smoke and other household odors such as toilet and kitchen odors arising from a variety of sources including pets and food wastes or odors from cooking foods, especially burning odors. The composition is especially useful for deodorizing fabrics such as curtains and upholstery fabrics.

SUMMARY OF THE INVENTION

The present invention includes a method of reducing oral malodor by providing a solution of sodium chlorite ($NaClO_2$) and a metal ion capable of complexing with sulfur, and applying the solution as a mouth rinse. The metal ion is preferably one that complexes with volatile sulfur compounds and carboxylic acids. Zinc is a most preferred ion, however, copper, silver or the metal ions may also be used.

DETAILED DESCRIPTION OF THE PREFERRED EMBODIMENTS

The present invention includes a method of reducing oral malodor comprising providing a mixture of sodium chlorite ($NaClO_2$) and a metal ion capable of complexing with sulfur and additionally carboxylic acids and amines. The mixture is applied as a mouth rinse for reducing components of oral malodor.

Sulfur compounds such as hydrogen sulfide ($H_2S$), methylmercaptan ($CH_3SH$) and di-methylmercaptan ($CH_3{}_2S$) are volatile compounds that are recognized as being major contributors to oral malodor. In most persons, hydrogen sulfide and methylmercaptan constitute over 90 percent of the total volatile sulfur content identified in mouth air. Numerous researchers have demonstrated that these volatile sulfur compounds are present in the head space and vapor of putrified saliva and in individual samples of mouth air.

Sodium chlorite has been used as an oral treatment, a deodorizing agent, an anti-plaque agent, a bacteriacide for treatment of gingivitis and as a bacterialcidal fungicidal and viralcidal agent. Sodium chlorite is quite soluble and is widely used as an industrial purification and oxidizing agent in the manufacture of wood pulp, water treatment and similar applications due to its bacterialcidal, disinfectant and sterilization qualities.

Sodium chlorite is also known by those skilled in the art as "stabilized chlorine dioxide". The sodium chlorite used in the present invention can be obtained from Bio-Cide International, Inc., International Dioxide, Vulcan Chemical and Christopfel & Saremi Consulting Laboratory, Inc.

The use of sodium chlorite and its effects on humans has been clinicly evaluated. The relative safety of oral ingestion of sodium chlorite has been demonstrated extensively in animals and in humans.

Sodium chlorite is known to oxidize hydrogen sulfide, methylmercapton and amines. Through oxidation, sodium chlorite reduces and eliminates odors caused by these compounds.

The preferred metal ion for complexing with the sulfur compounds and carboxylic acids is $Zn^{2+}$. Zinc is a nutrient and is non-toxic and is known to be safe for oral ingestion. Zinc has been used in mouth rinses and deodorants, however, its oral use in high concentrations has been limited due to its astringency and unpleasant taste. For purposes of the present invention, either zinc sulfate, zinc acetate, zinc citrate or zinc chloride are suitable sources of $Zn^{2+}$ ion.

Zinc coordinates with carboxylic acids, amines and sulfur containing compounds. Other metal ions useful in the present invention, although not specifically limited to, include copper and silver. What is important is that the metal ion coordinates with sulfur and/or carboxylic acids and/or amines to eliminate the compound as a component of oral malodor.

What has been found as surprising is that the combination of sodium chlorite and a metal ion such as zinc drastically reduces the components of oral malodor beyond what was believed to be possible with either stabilized chlorine dioxide or $Zn^{2+}$ alone. It has been found that approximately 500 to 1000 parts per million of sodium chlorite and approximately 200 to 500 parts per million $Zn^{2+}$ in combination perform as a very effective agent in reducing oral malodor.

Mixtures useful as mouth rinses were prepared using sodium chlorite alone, $Zn^{2+}$ alone, and both in combination. The mixtures were prepared in the order indicated in Tables 1 through 5. The pH of each mixture was monitored as the components were combined. Care was taken in controlling the pH of each mixture. A too low pH causes the sodium chlorite to disproportionate to a mix of $ClO_3{}^-$, $ClO_2$ and $Cl^-$ thereby making it unsuitable as a mouth rinse product for humans. A too high pH precipitates the zinc out of solution as $Zn(OH)_2$. Preferably, the pH should not go below 5.0 and in any event should never go below 4.0 to avoid affecting the sodium chlorite. The pH should be kept below approximately 9.0 to avoid precipitation of the zinc. Sodium citrate and citric acid are used to buffer the solution.

The ingredients used in the mixtures in Tables 1 through 5 were obtained from the following sources:

| Ingredient | Source |
|---|---|
| Sodium Citrate (Dihydrate) | Archer Daniels Midland Company |
| $ZnSO_4.7H_2O$ | Fisher Scientific Company |
| $NaClO_2$ | Christopfel & Saremi Consulting Laboratory, Inc. |
| Citric Acid | Fisher Scientific Company |
| Xylitol | Roquette America, Inc. |

The concentration of the $NaClO_2$ solution is reported in the industry as if it were a solution of $ClO_2$ with the same oxidizing equivalent. Therefore, 3.35% $NaClO_2$ solution is identified typically as 2% $ClO_2$. This convention is used in Tables 1–6 as set forth below.

TABLE 1

$ClO_2$ (1200 ppm)

| pH | Ingredient | Amount |
|---|---|---|
| 5.73 | Deionized Water | 924.67 gms |
| 8.16 | Sodium Citrate (Dihydrate) | 1.0 gms |
| 8.31 | $NaClO_2$ (2% $ClO_2$ Solution) | 60.0 gms |
| 6.67 | Citric Acid | Sufficient to adjust pH to 6.67 |
| 6.67 | Xylitol (Crystalline) | 14.3 gms |

TABLE 2

$Zn^{2+}$ (1000 ppm)

| pH | Ingredient | Amount |
|---|---|---|
| 5.78 | Deionized Water | 980.3 gms |
| 8.32 | Sodium Citrate (Dihydrate) | 1.0 gms |
| 5.92 | $ZnSO_4.7H_2O$ | 4.40 gms |
| 5.90 | Xylitol (Crystalline) | 14.3 gms |

TABLE 3

$ClO_2$ (610 ppm) $Zn^{2+}$ (300 ppm)

| pH | Ingredient | Amount |
|---|---|---|
| 6.29 | Deionized Water | 952.88 gms |
| 5.64 | $ZnSO_4.7H_2O$ | 1.32 gms |
| 6.26 | Sodium Citrate (Dihydrate) | 1.0 gms |
| 6.74 | $NaClO_2$ (2% $ClO_2$ Solution) | 30.50 gms |
| 6.36 | Xylitol (Crystalline) | 14.3 gms |

TABLE 4

$ClO_2$ (610 ppm) $Zn^{2+}$ (100 ppm)

| pH | Ingredient | Amount |
|---|---|---|
| 5.66 | Deionized Water | 953.8 gms |
| 5.50 | $ZnSO_4.7H_2O$ | 0.44 gms |
| 7.73 | Sodium Citrate (Dihydrate) | 1.0 gms |
| 7.74 | $NaClO_2$ (2% $ClO_2$ Solution) | 30.50 gms |
| 6.65 | Citric Acid | Sufficient to adjust pH to 6.65 |
| 6.65 | Xylitol (Crystalline) | 14.3 gms |

TABLE 5

$ClO_2$ (1200 ppm) $Zn^{2+}$ (1000 ppm)

| pH | Ingredient | Amount |
|---|---|---|
| 5.76 | Deionized Water | 920.3 gms |
| 5.53 | $ZnSO_4.7H_2O$ | 4.4 gms |
| 5.91 | Sodium Citrate (Dihydrate) | 1.0 gms |
| 6.39 | $NaClO_2$ (2% $ClO_2$ Solution) | 60.0 gms |
| 6.34 | Xylitol (Crystalline) | 14.3 gms |

Table 6 contains the results of Halimeter analysis of the mixtures of Tables 1 through 5. The Halimeter used was obtained from Interscan Corporation of Chatsworth, Calif., Model RH-17.

Two gas streams are connected by a "y" tube to give a stream of air containing an $H_2S$ concentration of approximately 300 to 500 parts per billion in the Halimeter. A gas cylinder containing $H_2S$ in nitrogen with its regulator pressure set at about 5 psi is the source of $H_2S$. The flow rate of the $H_2S$ containing gas is set at 50 ml/min which corresponds to a flow meter reading of 110. A small electric pump is used as the source of air, and the air flow rate is set at 1,000 ml/min which corresponds to a flow meter reading of 55.

The combined gas/air stream is passed through a bubbler that will hold the mixtures of Tables 1 through 5. The Halimeter is calibrated. Initially a control sample of deionized water was run and $H_2S$ levels in parts per billion were recorded at 1 minute, 2 minute, 3 minute, 4 minute and 5 minute intervals. Next, each of the mixtures of Tables 1 through 5 were placed in the bubbler and the emerging gas stream was then run through the Halimeter and the concentration of $H_2S$ was recorded at the same time intervals as the control sample, that is each minute for five minutes.

As can be seen from Table 6, the 1200 parts per million sodium chlorite mixture lowered the average value of $H_2S$ approximately 330 ppb while the 1000 parts per million $Zn^{2+}$ mixture lowered the $H_2S$ concentration on the average of 260 ppb.

The mixtures of Tables 3 and 4 wherein the concentration of sodium chlorite and $Zn^{2+}$ were reduced, while both were combined in a mixture, showed a further decrease in $H_2S$ concentration (See next two columns of Table 6). Of particular interest is the ability of the mixture of sodium chlorite and metal ion of the present invention to reduce the concentration of $H_2S$ much more than either the sodium chlorite alone or the zinc ion alone. For example, the mixture of Table 3 includes 610 parts per million of $ClO_2$ and 300 parts per million of $Zn^{2+}$, for a total of 910 parts per million combined active ions. This amount is less than the 1200 parts per million of sodium chlorite of Table 1 and 1000 parts per million of $Zn^{2+}$ alone of Table 2. Yet, the mixture of Table 3 unexpectedly reduces the concentration of $H_2S$ to a much lower level than either the mixture of Table 1 or Table 2. Similarly, the mixture of Table 4 which contains a total of 710 parts per million active ions of sodium chlorite and $Zn^{2+}$ shows a greater decrease in $H_2S$ than the $Zn^{2+}$ (1000 parts per million) mixture of Table 2 and only slightly less of a decrease than the $NaClO_2$ mixture (1,200 parts per million) of Table 1.

In the far right column of Table 6, a combination of 1200 parts per million of stabilized chlorine dioxide and 1000 ppm of $Zn^{2+}$ shows a dramatic decrease in $H_2S$ concentration.

TABLE 6

| $H_2S$ ppb at Various Time Intervals | Control Deionized Water | $ClO_2$ 1200 ppm | $Zn^{2+}$ 1000 ppm | $ClO_2$ 610 ppm $Zn^{2+}$ 300 ppm | $ClO_2$ 610 ppm $Zn^{2+}$ 100 ppm | $ClO_2$ 1200 ppm $Zn^{2+}$ 1000 ppm |
|---|---|---|---|---|---|---|
| 1 Minute | 473 | 177 | 254 | 115 | 218 | 87 |
| 2 Minute | 503 | 180 | 258 | 115 | 225 | 82 |
| 3 Minute | 515 | 190 | 257 | 119 | 229 | 80 |
| 4 Minute | 547 | 191 | 258 | 125 | 248 | 80 |
| 5 Minute | 546 | 196 | 257 | 129 | 242 | 81 |
| Average | 517 | 187 | 257 | 121 | 232 | 82 |

Although the present invention has been described with reference to preferred embodiments, workers skilled in the art will recognize that changes may be made in form and detail without departing from the spirit and scope of the invention.

What is claimed is:

1. A method of reducing oral malodor comprising preparing a solution of $NaClO_2$ and a zinc salt and applying the solution as a mouth rinse, wherein the concentration of $NaClO_2$ in the solution is between approximately 500 and 1000 parts per million, wherein the zinc salt ionizes in the solution to produce $Zn^{2+}$, and wherein the concentration of $Zn^{2+}$ in the solution is between approximately 200 and 500 parts per million.

2. The method of claim 1 wherein the $NaClO_2$ is at a concentration effective against oral malodor.

3. The method of claim 1 wherein the $Zn^{2+}$ is in an amount that is effective against oral malodor.

\* \* \* \* \*